(12) United States Patent
Goto et al.

(10) Patent No.: US 10,067,087 B2
(45) Date of Patent: Sep. 4, 2018

(54) BIOMOLECULE ANALYZER

(71) Applicant: Sharp Life Science Corporation, Kobe, Hyogo (JP)

(72) Inventors: Shinichi Goto, Sakai (JP); Hideki Kinoshita, Sakai (JP); Mieko Hirabayashi, Sakai (JP); Kouhei Kageyama, Sakai (JP); Taiga Tominaga, Sakai (JP)

(73) Assignee: SHARP LIFE SCIENCE CORPORATION, Kobe, Hyogo (JP)

( * ) Notice: Subject to any disclaimer, the term of this patent is extended or adjusted under 35 U.S.C. 154(b) by 20 days.

(21) Appl. No.: 15/303,551

(22) PCT Filed: Nov. 19, 2015

(86) PCT No.: PCT/JP2015/082490
§ 371 (c)(1),
(2) Date: Oct. 12, 2016

(87) PCT Pub. No.: WO2016/080476
PCT Pub. Date: May 26, 2016

(65) Prior Publication Data
US 2017/0038336 A1    Feb. 9, 2017

(30) Foreign Application Priority Data
Nov. 20, 2014 (JP) .................. 2014-235992

(51) Int. Cl.
*G01N 27/453* (2006.01)
*G01N 27/447* (2006.01)

(52) U.S. Cl.
CPC . *G01N 27/44739* (2013.01); *G01N 27/44704* (2013.01); *G01N 27/44747* (2013.01); *G01N 27/44726* (2013.01)

(58) Field of Classification Search
CPC ................................. G01N 27/44739
See application file for complete search history.

(56) References Cited

U.S. PATENT DOCUMENTS

| 4,631,120 A | 12/1986 | Pohl |
| 4,812,216 A | 3/1989 | Hurd et al. |
| 5,234,559 A | 8/1993 | Collier et al. |
| 5,916,429 A | 6/1999 | Brunk |

(Continued)

FOREIGN PATENT DOCUMENTS

| GB | 2450841 A | 1/2009 |
| JP | 01-112147 A | 4/1989 |

(Continued)

OTHER PUBLICATIONS

English language translation of the Written Opinion for International application No. PCT/JP2015/082490 (Year: 2016).*

*Primary Examiner* — Alexander Stephan Noguerola
(74) *Attorney, Agent, or Firm* — ScienBiziP, P.C.

(57) ABSTRACT

A biomolecule analyzer (100) includes an arm part (20-23, 66) retaining a transfer membrane (1) that is arranged at a position opposing a first opening (50*a*), and a drive unit (62-65) that is provided below an anode buffer tank (30), and drives the arm part in a substantially horizontal direction, in which the arm part passes along outer sides of side walls of the anode buffer tank (30), wraps around upper ends of the side walls and links at inner walls of the side wall.

14 Claims, 10 Drawing Sheets

(56) References Cited

U.S. PATENT DOCUMENTS

2009/0127118 A1* 5/2009 Unuma ............ G01N 27/44717
                                                    204/641
2014/0224657 A1   8/2014 Kusumoto et al.

FOREIGN PATENT DOCUMENTS

| JP | 64-91049 A | 4/1989 |
| JP | 2007-292616 A | 11/2007 |
| WO | 2011/106693 A2 | 9/2011 |

* cited by examiner

BIOMOLECULE ANALYZER

TECHNICAL FIELD

The present invention relates to a device that analyzes biomolecules, and in more detail, relates to a device that transfers biomolecules separated by electrophoresis to a transfer membrane.

BACKGROUND ART

Patent Documents 1 and 2 describe devices that perform electrophoresis on biomolecules such as DNA and proteins in gel, and transfer from a gel edge face to a direct transfer membrane (hereinafter such a device may also be referred to as "direct-blot electrophoresis-transfer device").

The devices described in Patent Documents 1 and 2 are horizontal devices that include: a gel arranged in a horizontal direction, a gel frame accommodating this gel, a cathode buffer tank and anode buffer tank that respectively connect with both ends of this gel, a transfer membrane that faces one end of this gel, a rectangular transfer membrane frame that fixes this transfer membrane, and a vertical conveying mechanism that conveys the transfer membrane frame in the vertical direction. This horizontal device transfers DNA, etc. separated on the gel to the transfer membrane, by raising the transfer membrane using the vertical conveying mechanism, while performing electrophoresis on the gel.

Patent Document 1: U.S. Pat. No. 5,234,559 (registration date: 1993 Aug. 10)

Patent Document 2: U.S. Pat. No. 5,916,429 (registration date: 1999 Jun. 29)

DISCLOSURE OF THE INVENTION

Problems to be Solved by the Invention

However, with the horizontal devices according to conventional technology, the gel frame is provided in the horizontal direction, and the transfer membrane is raised in the vertical direction (such as configuration is also referred to as "horizontal-type" in the present specification). With the above-mentioned horizontal device, since the top surface of the gel frame contacts with the atmosphere, and the bottom face of the gel frame contacts with the structure of the device; the cooling of the gel frame becomes insufficient, and the gel may generate heat during electrophoresis. When the gel generates heat, there is a risk of defects such as the electrophoresis pattern warping, separability declining, and the separated DNA, etc. not being transferred to the transfer membrane. In addition, the transfer membrane is a generally thin plastic film, and has elasticity. For this reason, the membrane fixed to the rectangular transfer membrane frame enters a state in which the center tends to stretch more than the periphery part, and tensile strength more strongly acts as approaching the edges. For this reason, in the vicinity of the center, there is a risk of the transfer pattern warping.

Therefore, the present inventors reviewed vertical-type devices having a unique configuration, based on a unique concept. With the vertical device, the separation unit accommodating the separation medium such as gel is standing in the substantially vertical direction (such a configuration is also referred to as "vertical type" in the present specification). With the above-mentioned vertical device, since the upper part of the separation unit contacts with the cathode buffer, and the lower part of the separation unit contacts with the anode buffer, it is possible to sufficiently cool the separation unit by liquid-cooling. In addition, the transfer membrane can be conveyed without fixing to a rectangular transfer membrane frame.

However, with the above-mentioned vertical device, it is necessary to cause the transfer membrane to move in a substantially horizontal direction within the anode buffer tank. Herein, as in the horizontal device according to conventional technology, in a case of trying to arrange the transfer membrane conveying mechanism upstream of the transfer membrane, there is a risk of the buffer solution spattering from the anode buffer tank causing the durability of the transfer membrane conveying mechanism to decline, and a risk of the transfer membrane conveying mechanism becoming an obstruction to the various operations on the above-mentioned vertical device.

The present invention has been made taking account of the above-mentioned problems, and has a main object of providing a vertical-type direct-blot electrophoresis transfer device including a suitable transfer-membrane conveying mechanism.

Means for Solving the Problems

In order to solve the above-mentioned problems, a biomolecule analyzer according to one aspect of the present invention includes: a first buffer solution tank; a second buffer solution tank that is disposed above the first buffer solution tank; a separation unit in which a separation medium is stored, having a first opening that opens within the first buffer solution tank and a second opening that opens within the buffer solution tank, and standing up in a substantially vertical direction; an arm part that retains a transfer membrane disposed at a position opposing the first opening; and a drive unit that is provided under the first buffer solution tank, and drives the arm part in a substantially horizontal direction, in which the arm part passes along outer sides of side walls of the first buffer solution tank, wraps around upper ends of the side walls, and links at inner sides of the side walls.

According to the above-mentioned configuration, by establishing a configuration in which the separation unit stands up substantially vertically, it is possible for the separation unit to be immersed in buffer solution in the first or second buffer solution tank to liquid-cool the separation medium. However, in the case of configuring the biomolecule analyzer in this way, it is necessary to make the transfer membrane move within the first buffer solution tank.

Herein, according to the above-mentioned configuration, by providing the drive unit under the first buffer solution tank, and making the form of the arm part into a form that passes along the outer sides of the side walls of the first buffer solution tank, wraps around the top ends of the side walls and then links at the inner sides of the side walls, it is possible to cause the transfer membrane to move successfully within the first buffer solution tank, while avoiding a decline in the durability of the drive unit due to the buffer solution and the hindrance of various operations by the drive unit. It is thereby possible to provide a vertical-type direct-blot electrophoresis-transfer device including a suitable transfer-membrane conveying mechanism.

With the biomolecule analyzer according to one aspect of the present invention, the transfer membrane may have a first end that is forward in a movement direction according to driving of the arm part and a second end that is rearward in the movement direction, and the arm part may include a first fixing part that fixes the first end, a second fixing part that fixes the second end, and an elastic body that biases the first fixing part and the second fixing part in directions facing away from each other.

If a state in which the transfer membrane is loose, when causing the transfer membrane to move, the interval between the transfer membrane and first opening may become large, and the transfer result may be blurred.

According to the above-mentioned configuration, since the first and second fixing parts that fix both ends in the movement direction of the transfer membrane are biased in directions facing away from each other, it is possible to impart a constant tension to the transfer membrane. It is thereby possible to establish the transfer membrane in a tightened state, and thus able to obtain favorable transfer results.

With the biomolecule analyzer according to one aspect of the present invention, a support member for supporting the transfer membrane from an opposite side of the transfer membrane to the separation unit may be provided at a bottom part of the first buffer solution tank, and the transfer membrane may be bent by the separation unit so that an opposite side to the separation unit becomes convex.

According to the above-mentioned configuration, the transfer membrane is supported by the support member, and the separation unit pushes this down to be bent so as to become convex downward (opposite side to the separation unit). Tension thereby acts on the transfer membrane, whereby it is possible to cause the transfer membrane to closely contact the first opening. In particular, since the transfer membrane is maintained in a state tightened by the elastic body, it is possible to satisfactorily press the transfer membrane against the first opening. It is thereby possible to more satisfactorily perform transfer from the separation medium to the transfer membrane.

With the biomolecule analyzer according to one aspect of the present invention, the support member may be formed on the bottom part at positions to form a pair interposing a position opposing the first opening.

According to the above-mentioned configuration, the transfer membrane is supported by support members arranged at both sides of the separation unit, and the separation unit pushes this down to be bent so as to become convex downward (opposite side to the separation unit). Tension thereby more uniformly acts on the transfer membrane, whereby it is possible to cause the transfer membrane to closely contact the first opening more uniformly. It is thereby possible to more suitably perform transfer from the separation medium to the transfer membrane.

With the biomolecule analyzer according to one aspect of the present invention, the transfer membrane may have a first end that is forward in a movement direction according to driving of the arm part, and a second end that is rearward in the movement direction, and the arm part may include a first fixing part that fixes the first end, a second fixing part that fixes the second end, and a connection part that connects the first fixing part and the second fixing part to be separated by a predetermined distance.

According the above-mentioned configuration, by fixing the first and second ends of the transfer membrane by the first and second fixing parts, respectively, which are connected to be separated by a predetermined distance, it is possible to tighten the transfer membrane without slack along the movement direction thereof. It is thereby possible to suppress the transfer results from blurring due to slack in the transfer membrane, and thus improve the measurement sensitivity.

With the biomolecule analyzer according to one aspect of the present invention, the connection parts may be disposed at positions to interpose the transfer membrane from lateral sides relative to the movement direction.

According to the above-mentioned configuration, it is possible to avoid the connection part from overlapping the top surface (face opposing the first opening) and back surface (face on opposite side to the first opening) of the transfer membrane. It is thereby possible to prevent the transfer from the separation medium to the transfer membrane, abutting of other members to the back surface of the transfer membrane, etc. from being inhibited by the connection part.

With the biomolecule analyzer according to one aspect of the present invention, a support member that supports the transfer membrane from an opposite side to the separation unit of the transfer membrane may be provided to a bottom part of the first buffer solution tank, and the transfer membrane may be bent by the separation unit so that an opposite side to the separation unit becomes convex.

According to the above-mentioned configuration, the transfer membrane is supported by the support member, and the separation unit pushes this down to be bent so as to become convex downward (opposite side to the separation unit). Tension thereby acts on the transfer membrane, whereby it is possible to cause the transfer membrane to closely contact the first opening. It is thereby possible to more satisfactorily perform transfer from the separation medium to the transfer membrane.

With the biomolecule analyzer according to one aspect of the present invention, the support members may be respectively formed on the bottom part to form a pair at positions interposing a position that opposes the first opening.

According to the above-mentioned configuration, the transfer membrane is supported by the support members arranged at both sides of the separation unit, and the separation unit pushes this down to be bent so as to become convex downward (opposite side to the separation unit). Tension thereby more uniformly acts on the transfer membrane, whereby it is possible to cause the transfer membrane to closely contact the first opening more uniformly. It is thereby possible to more suitably perform transfer from the separation medium to the transfer membrane.

With the biomolecule analyzer according to one aspect of the present invention, a slope angle of the transfer membrane from a position contacting the support member until a position contacting the first opening may be at least 1° and no more than 60° downwards relative to a horizontal plane.

According to the above-mentioned configuration, it is possible to appropriately adjust the tension acting on the transfer membrane to more suitably perform transfer from the separation medium to the transfer membrane.

With the biomolecule analyzer according to one aspect of the present invention, a portion of the arm part that wraps around the upper ends of the side walls may be detachable from the drive unit, and the first buffer solution tank may be detachable from the biomolecule analyzer.

According to the above-mentioned configuration, by being able to remove the first buffer solution tank, it is possible to easily wash the first buffer solution tank, without cleaning solution, etc. adhering to the drive unit. In addition, upon removing the first buffer solution tank, since it is possible to separate, from the drive unit, a portion of the arm part that wraps around the upper ends of the side walls of the first buffer solution tank to link at inner sides of the side walls, the first buffer solution tank can be easily removed.

With the biomolecule analyzer according to one aspect of the present invention, the arm part may be linked to the drive unit, and may have a first portion extending at outer sides of the side walls until a position aligning with upper ends of the side walls, and a second portion that fits with the first portion, and extends to an inner side of the side walls by spanning the upper ends of the side walls.

According to the above-mentioned configuration, the second portion can be easily detached and attached relative to the drive unit. The first portion is arranged at the outer sides of the side walls of the first buffer solution tank, and thus will not become a hindrance to removal of the first buffer solution tank and various operations such as setting of the electrode. For this reason, it is possible to successfully perform various operations by unfastening the second portion as appropriate.

With the biomolecule analyzer according to one aspect of the present invention, the first buffer solution tank, the second buffer solution tank and the separation unit may be transparent.

According to the above-mentioned configuration, it is possible to observe the states of the separation medium and transfer membrane during operation of the device. It is thereby possible to confirm the movement of the visible marker by the naked eye, for example.

With the biomolecule analyzer according to one aspect of the present invention, a first electrode may be disposed in the first buffer solution tank, a second electrode may be disposed in the second buffer solution tank, and the transfer membrane may be disposed so as to be interposed between the first opening and the first electrode.

According to the above-mentioned configuration, since it is possible to apply voltage between the first opening that opens within the first buffer solution tank and the second opening that opens within the second buffer solution tank, electrophoresis of biomolecules can be successfully performed. In addition, since the transfer membrane is interposed between the first opening and the first electrode, it is possible to successfully perform transfer of the separated biomolecules from the first opening to the transfer membrane.

With the biomolecule analyzer according to one aspect of the present invention, the separation unit may be mounted to be detachable relative to the second buffer solution tank, and the second buffer solution tank may be mounted to be detachable relative to the first buffer solution tank.

According to the above-mentioned configuration, since it is possible to remove the separation unit and second buffer solution tank, the separation unit and second buffer solution tank can be easily washed without cleaning solution, etc. adhering to the drive unit.

Effects of the Invention

According to the present invention, it is possible to provide a vertical-type direct-blot electrophoresis-transfer device including a suitable transfer-membrane conveying mechanism.

PREFERRED MODE FOR CARRYING OUT THE INVENTION

First Embodiment

An embodiment of the present invention is as follows when explained based on the drawings.

Figure 1:
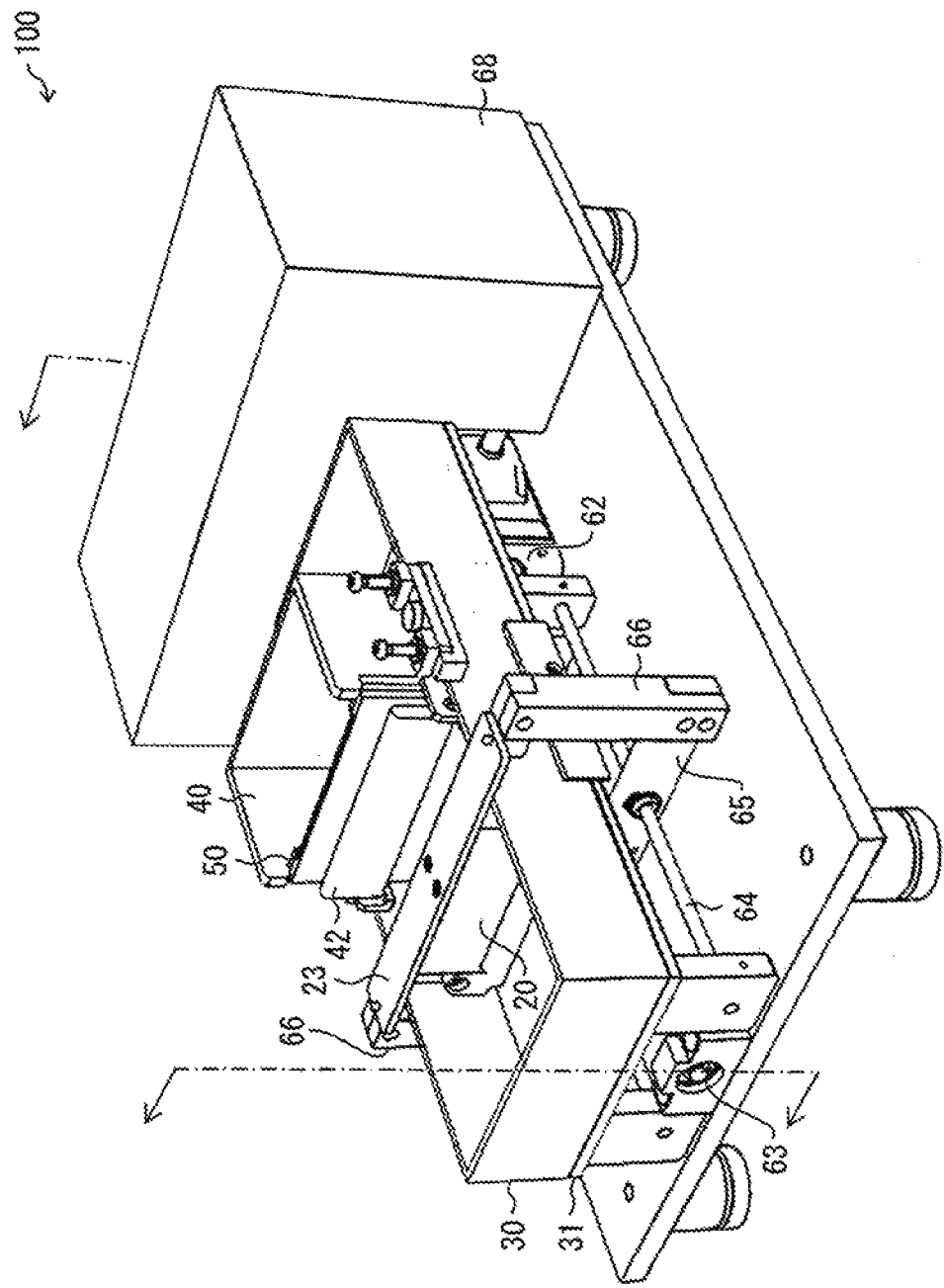
FIG. 1 is a perspective view showing an outline configuration of a biomolecule analyzer according to one embodiment of the present invention.
Figure 2:
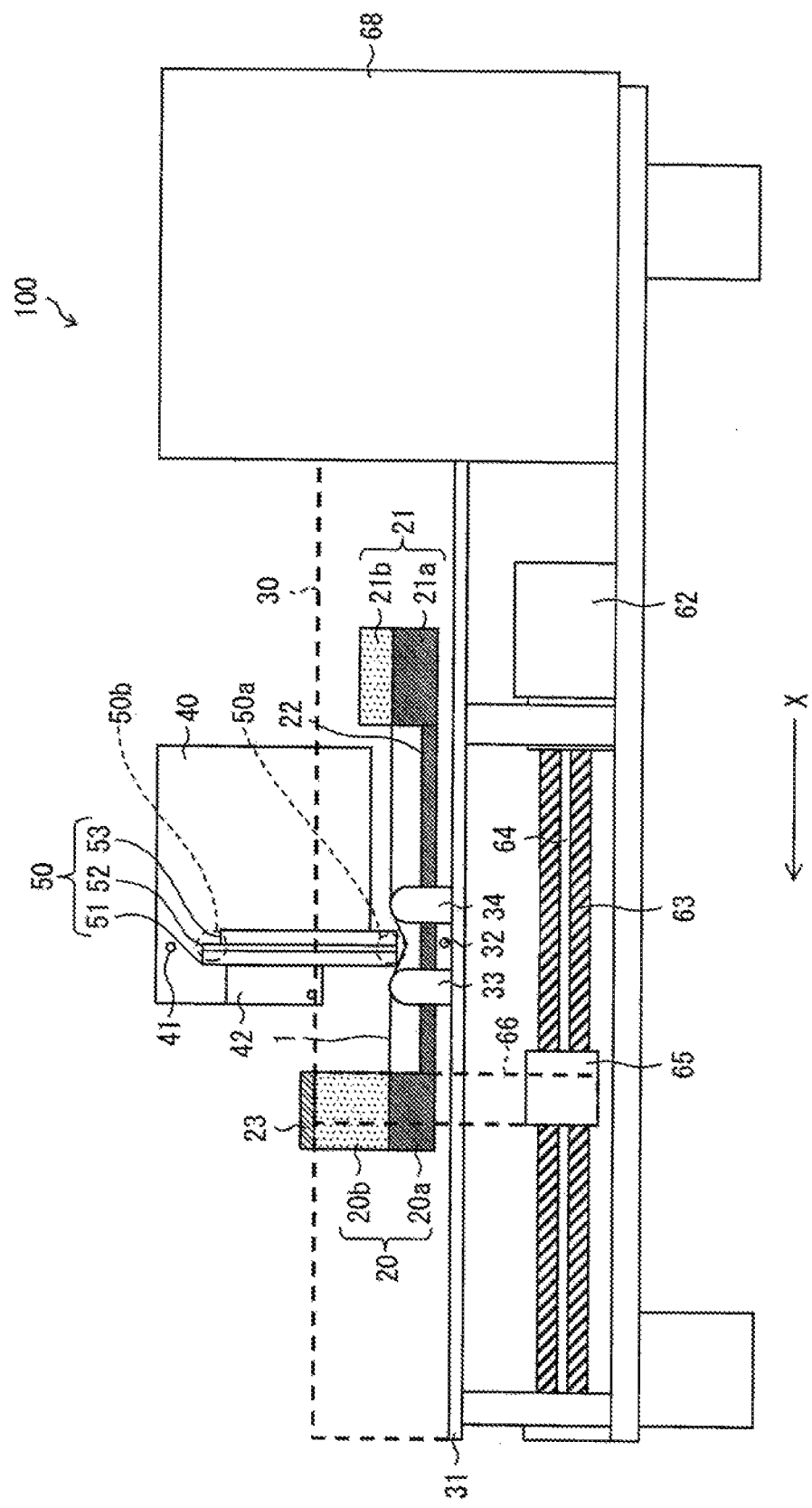
FIG. 2 is a cross-sectional view showing an outline configuration of a biomolecule analyzer according to an embodiment of the present invention.

First, an outline configuration of a biomolecule analyzer 100 according to the present embodiment will be explained by referencing FIGS. 1 and 2. FIG. 1 is a perspective view approximately showing the configuration of the biomolecule analyzer 100. FIG. 2 is a lateral cross-sectional view approximately showing the configuration of the biomolecule analyzer 100.

As shown in FIGS. 1 and 2, the biomolecule analyzer 100 is a vertical-type direct-blot electrophoresis-transfer device, and includes a clamp (arm part, first fixed part) 20, clamp (arm part, second fixed part) 21, clamp frame (arm part, connection part) 22, carrier (arm part, portion wrapping around upper end of side wall, second portion) 23, anode buffer tank (first buffer solution tank) 30, table 31, cathode buffer tank (second buffer solution tank) 40, separation unit 50, motor (drive part) 62, ball screw (drive part) 63, guide shaft (drive part) 64, shaft holder (drive part) 65, guide pole (arm part, first portion) 66, and controller unit 68. In addition, although not illustrated for explanation, a lid covering the entirety during operation is further included for safety.

Herein, the separation unit 50 accommodates separation gel (separation medium) 52, and has a first opening 50a that opens within the anode buffer tank 30 and a second opening 50b that opens within a cathode buffer tank 40. In addition, a transfer membrane 1 is arranged inside of the anode buffer tank 30 so as to face the first opening 50a. Furthermore, the anode (first electrode) 32 is arranged within the anode buffer tank 30, and the cathode (second electrode) 41 is arranged within the cathode buffer tank 40.

For this reason, with the biomolecule analyzer 100, the cathode 41 within the cathode buffer tank 40 and the anode 32 within the anode buffer tank 30 are electrically connected via the buffer solutions of the two tanks, separation gel 52 and transfer membrane 1, by filling buffer solutions into the cathode buffer tank 40 and anode buffer tank 30. In other words, the biomolecule analyzer 100 is a device that separates a sample introduced from the second opening 50b by way of the separation gel 52 and causes each separated component to be dispensed from the first opening 50a and adsorb to the transfer membrane 1, by applying a voltage between the cathode 41 and anode 32.

Hereinafter, the respective principle members will be explained in detail by referencing FIGS. 1 and 2.
(Anode and Cathode)

The anode 32 is arranged within the anode buffer tank 30, and the cathode 41 is arranged within the cathode buffer tank 40. The anode 32 and cathode 41 are formed from a material having electrical conductivity such as a metal. As the material forming the anode 32 and cathode 41, for example, platinum is preferably from the viewpoint of suppressing ionization of the electrodes.

The electrode arrangements of these are not particularly limited so long as the anode 32 is arranged within the anode buffer tank 30 and the cathode 41 is arranged within the cathode buffer tank 40; however, for example, the cathode 41, first opening 50a and anode 32 may be arranged on substantially the same straight line. In such an arrangement, so long as the transfer membrane 1 is arranged as shown in FIG. 1, the precision of sample adsorption can be improved since the line of electric force passing through the first opening 50a will be substantially vertical relative to the transfer membrane 1.

In addition, the anode 32 is preferably arranged to be distanced from the transfer membrane 1. It is thereby possible to suppress bubbles generating from the anode 32 from negatively influencing the adsorption of separation components on the transfer membrane 1.

The anode 32 and cathode 41, for example, may be used by connecting to the control unit 68, or may be used by connecting to an external power supply (DC power source). In the case of using by connecting to an external power supply, after setting the time, current and voltage in the power supply, the control unit 68 may be operated to cause the biomolecule analyzer 100 to start operation at the same time as operation initiation of the power supply.
(Anode Buffer Tank and Cathode Buffer Tank)

The anode buffer tank 30 and cathode buffer tank 40 are insulative containers storing the buffer solution (buffer). The cathode buffer tank 40 is provided above the anode buffer tank 30. It should be noted that, in the present embodiment, the anode buffer tank 30 is fixed on the table 31, and the cathode buffer tank 40 is fixed to the anode buffer tank 30; however, the present invention is not limited to this configuration.

The buffer solutions filled in the anode buffer tank 30 and cathode buffer tank 40 can be any buffer solution having electrical conductivity, and particularly, a buffer solution having a buffering portion of weakly acidic to weakly basic can be suitably used. As such a buffer solution, for example, it is possible to use buffer solutions such as a Tris/glycine-based buffer solution, acetic acid buffer solution, sodium carbonate-based buffer solution, CPS buffer solution, Tris/boric acid/EDTA buffer solution, Tris/acetic acid/EDTA buffer solution, MOPS, phosphoric acid buffer solution, and Tris/tricine-based buffer solution.

In addition, although the details are described later, guides (support members) 33, 34 supporting the transfer membrane 1 from the back surface of the transfer membrane 1 (face on an opposite side to the separation unit 50) are provided to the bottom part of the anode buffer tank 30 in the movement path of the transfer membrane 1.

(Separation Unit)

The separation unit 50 stores the separation gel (separation medium) 52 inside thereof. In the present embodiment, the separation unit 50 is standing in a substantially vertical direction, and the lower part thereof is arranged within the anode buffer tank 30, and the upper part thereof is arranged so that one side contacts the cathode buffer tank 40. The separation gel 52 is thereby liquid-cooled by at least one of the buffer solution within the anode buffer tank 30 and the buffer solution within the cathode buffer tank 40, and can be sufficiently cooled.

In addition, the separation unit 50 has the first opening 50a that opens within the anode buffer tank 30, and the second opening 50b that opens within the cathode buffer tank 40. It thereby comes to be so that the separation gel 52 faces inside the anode buffer tank 30 via the first opening 50a, and faces inside the cathode buffer tank 40 via the second opening 50b. It should be noted that, in the present embodiment, the separation unit 50 is fixed to the cathode buffer tank 40 by the lock 42 provided to the cathode buffer tank 40; however, the present invention is not limited to this configuration.

The separation unit 50 can be configured from two insulating plates 51, 53 formed from insulators such as glass or acrylic. In one embodiment, the separation unit 50 exposes the separation gel 52 by a part of the insulating plate 53 being notched out at the second opening 50b, whereby sample can be easily introduced to the separation gel 52.

The separation gel 52 is a gel for separating the sample components introduced from the second opening 50b according to the molecular weight. The separation gel 52 can be filled into the separation unit 50 prior to installation of the separation unit 50 to the biomolecule analyzer 100, or after installing. In addition, a commercially available PAGE chip into which the separation gel 52 is filled may be used as the separation unit 50. As an example of the separation gel 52, acrylamide gel, agarose gel and the like are exemplified. The width of the separation gel 52 can be established as a length enabling a 10- to 12-lane sample to be separated, for example.

It should be noted that, in the present embodiment, although the configuration filling the separation gel 52 into the separation unit 50 is being adopted, a configuration providing multiple ultrafine posts called nano-pillars between the insulating plate 51 and insulating plate 53 can also be adopted.

It addition, the first opening 50a of the separation unit 50 may be covered by a coating part formed by an electrically conductive porous material (hydrophilic PVDF (polyvinylidene difluoride) film), hydrophilic PTFE (polytetrafluoroethylene) film, etc.), including the circumference thereof. In the case of the transfer membrane 1 contacting or being pushed against the first opening 50a (case of not providing a distance between the first opening 50a and transfer membrane 1), the transfer membrane 1 can reduce the frictional resistance and damage incurred from the separation unit 50 and separation gel 52 when the transfer membrane 1 is conveyed.

It should be noted that, by the separation unit 50 standing in a substantially vertical direction, the separation unit 50 can greatly increase the sample introduction amount compared to a configuration being installed in a substantially horizontal direction. This is because, with the horizontal-type electrophoresis apparatus, it is difficult to change the depth of the well provided in the separation gel; however, with the vertical-type electrophoresis apparatus, since the depth of the well can be changed easily, the sample introduction amount can be made to increase easily.

(Transfer Membrane 1)

It is preferable for the transfer membrane 1 to be an absorbing/retaining body of samples that enables to stably preserve a sample separated by the separation gel 52 over a long period, and further, facilitates subsequent analysis. As the material of the transfer membrane 1, it is preferably a material having high strength, and having high sample binding capacity (adsorbable weight per unit volume). As the transfer membrane 1, a PVDF membrane or the like is suited in the case of the sample being protein. It should be noted that it is preferable to perform hydrophilization treatment using methanol or the like in advance on the PVDF membrane. Otherwise, a membrane conventionally used in the adsorption of proteins, DNA and nucleic acids such as a nitrocellulose membrane or nylon membrane can also be used.

It should be noted that, the samples that can be separated and adsorbed in the biomolecule analyzer 100 are not particularly limited to these; however, a preparation from biological material (e.g., biont, body fluid, cell strain, tissue culture, or tissue fragment), a commercially available reagent, and the like can be exemplified. For example, polypeptides or polynucleotides can be exemplified.

The transfer membrane 1 is used in a state immersed in the buffer solution within the anode buffer tank 30.

In the present embodiment, the transfer membrane 1 is sufficient so long as having a length used in one-time electrophoresis/transfer, i.e. length of a distance moving within the anode buffer tank 30 in the one-time electrophoresis/transfer. By configuring the transfer membrane 1 in this way, an operation to cut the transfer membrane 1 for every one-time electrophoresis/transfer becomes unnecessary, and thus the usability of the biomolecule analyzer 100 can be improved. In addition, the width of the transfer membrane 1 is sufficient so long as established as a length corresponding to the width of the separation gel 52.

(Arm Part)

In the present embodiment, the transfer membrane 1 is used in a state retained by the arm part for movement thereof and maintenance of the relative position with the first opening 50a. In the present embodiment, the arm part is configured from clamps 20, 21, a clamp frame 22, a carrier 23 and a guide pole 66, which are a series of coupled members. Thereamong, the structure configured from the clamps 20, 21 and clamp frame 22 is also referred to as adjuster. The adjuster is arranged at an inner side of a side wall of the anode buffer tank 30. In addition, FIG. 3 is a perspective view showing an outline structure of the adjuster. As shown in FIG. 3, the clamp 20 is configured from a lower part 20a and an upper part 20b, and the clamp 21 is configured from a lower part 21a and an upper part 21b.

Figure 3A:
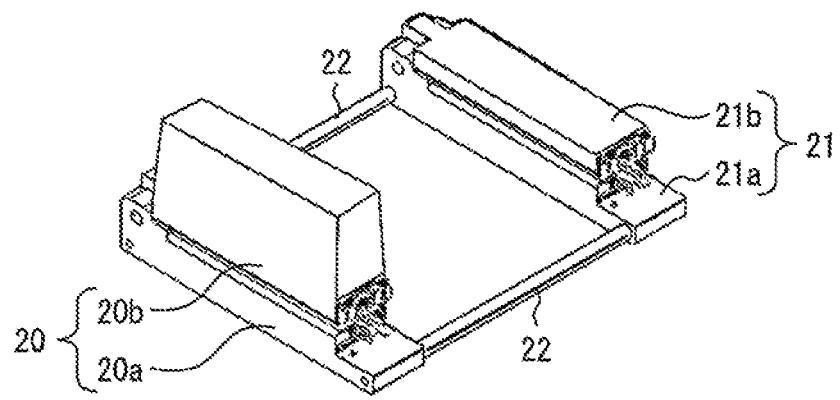
FIG. 3 is a perspective view showing an outline configuration of an adjuster in an embodiment of the present invention.
Figure 3B:
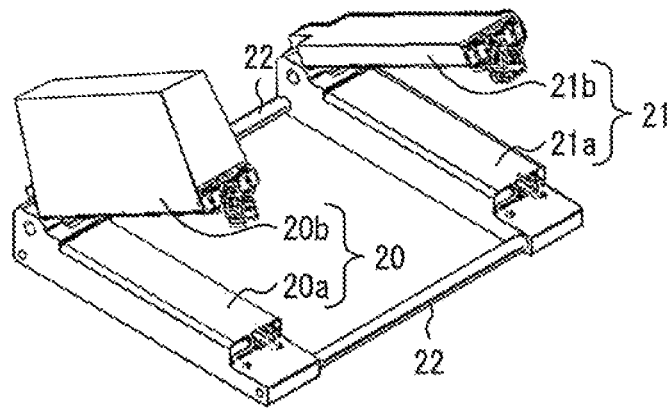

As shown in FIG. 3(b), between the lower part 20a and upper part 20b, and between the lower part 21a and upper part 21b each come to be open. In this state, after sandwiching the end (first end) forward in the movement direction of the transfer membrane 1 between the lower part 20a and upper part 20b, and sandwiching the end (second end) rearward in the movement direction of the transfer membrane 1 between the lower part 21a and upper part 21b, by closing each of between the lower part 20a and upper part 20b and between the lower part 21a and upper part 21b as shown in FIG. 3(a), it is possible to fix the end forward in the movement direction of the transfer membrane 1 by the clamp 20 and fix the end rearward in the movement direction of the transfer membrane 1 by the clamp 21. The arm part can thereby retain the transfer membrane 1. It should be noted that the clamps 20, 21 may include a lock for fixing in a closed state.

The clamp frame 22 is a shaft member connecting the clamps 20, 21, and connects the clamps 20, 21 to be separated by a predetermined distance. It is thereby possible to tighten the transfer membrane 1 without slack along the movement direction thereof, when fixing both ends of the transfer membrane 1 by the clamps 20, 21. It is thereby possible to suppress the transfer results from blurring due to slack in the transfer membrane 1, and thus improve the measurement sensitivity. In addition, it is possible to make the tension acting on the transfer membrane 1 conveyed accompanying movement of the clamp 20 to be constant. Therefore, it is possible to more suitably transfer a sample to the transfer membrane 1 without blurring. However, it may be a configuration omitting the clamp 21 and clamp frame 22.

The clamp frame 22 is arranged at a position sandwiching the transfer membrane 1 from the lateral side to the movement direction, whereby it is possible to avoid the clamp frame 22 from overlapping the top surface (face opposing the first opening 50a) and back surface (facing on opposite side to first opening 50a) of the transfer membrane 1. It is thereby possible to prevent transfer from the separation gel 52 to the transfer membrane 1, abutting of other members with the back surface of the transfer membrane 1, etc. (details described later) being inhibited by the clamp frame 22.

The guide pole 66 is a shaft member that is arranged so as to connect to a drive unit described later (shaft holder 65), and pass to outside of a side wall of the anode buffer tank 30. The carrier 23 is a member that connects to the guide pole 66, and connects to the clamp 20 by going around the upper end of the side wall of the anode buffer tank 30.

In the above way, the arm part passes along the outer sides of the side walls of the anode buffer tank 30 from a position connecting to the drive unit, wraps around the upper ends of the side walls, and links at the inner sides of the side walls.

It should be noted that, although not to limit the present invention, in the present embodiment, the guide poles 66 extend at outer sides of the side walls of the anode buffer tank 30 until positions aligning with the upper ends of the side walls. Then, the carrier 23 fits together with the guide poles 66, and extends to an inner side of the side wall by spanning over the upper ends of the side walls of the anode buffer tank 30.

By configuring in this way, the carrier 23 can attach and detach easily to the drive unit. The guide poles 66 are arranged at the outer side of the side walls of the anode buffer tank 30, and do not become obstructions to various operations such as detachment of the anode buffer tank 30 (details explained in second embodiment), or setting of electrodes, which are performed as necessary. For this reason, it is possible to successfully perform various operations by removing the carrier 23 as appropriate.

(Drive Unit)

The drive unit drives the arm part in a substantially horizontal direction, and is configured by a motor 62, ball screw 63, guide shaft 64 and shaft holder 65 in the present embodiment.

The motor 62 causes the ball screw 63 to rotate. The motor 62 may employ one that can vary rotation speed, and may employ one of fixed rotation speed in combination with gears. The ball screw 63 threads with the shaft holder 65 along with penetrating the shaft holder 65. The guide shaft 64 penetrates the shaft holder 65, and the shaft holder 65 is configured to be movable along the guide shaft 64. Then, by the motor 62 causing the ball screw 63 to rotate, the shaft holder 65 is driven in the X direction in the drawing (substantially horizontal direction). The shaft holder 65 connects with the arm part (guide pole 66), whereby the drive unit can drive the arm part in the X direction in the drawing (substantially horizontal direction). Then, due to the arm part retaining the transfer membrane 1, the transfer membrane 1 moves in the X direction in the drawing (substantially horizontal direction).

However, the present invention is not limited thereto, and so long as being able to drive the arm part in a substantially horizontal direction, the drive unit may be configured by another drive mechanism (e.g., belt, gears, etc.).

In addition, the drive unit is provided below the anode buffer tank 30. It is thereby possible to prevent the risk of the buffer solution having scattered from the anode buffer tank 86 from causing the durability of the drive unit to decline, and the risk of the drive unit becoming a hindrance to various operations on the biomolecule analyzer 100.

(Control Unit)

The control unit 68 is a control panel that performs various controls of the biomolecule analyzer 100 (control of the position of the arm part, control of current/voltage applied to the anode 32 and cathode 41, etc.). The control unit 68 may include buttons and switches for receiving inputs from a user, and lamps, a display unit, etc. for notifying the operating state to the user.

(Electrophoresis and Transfer of Sample)

Figure 4:
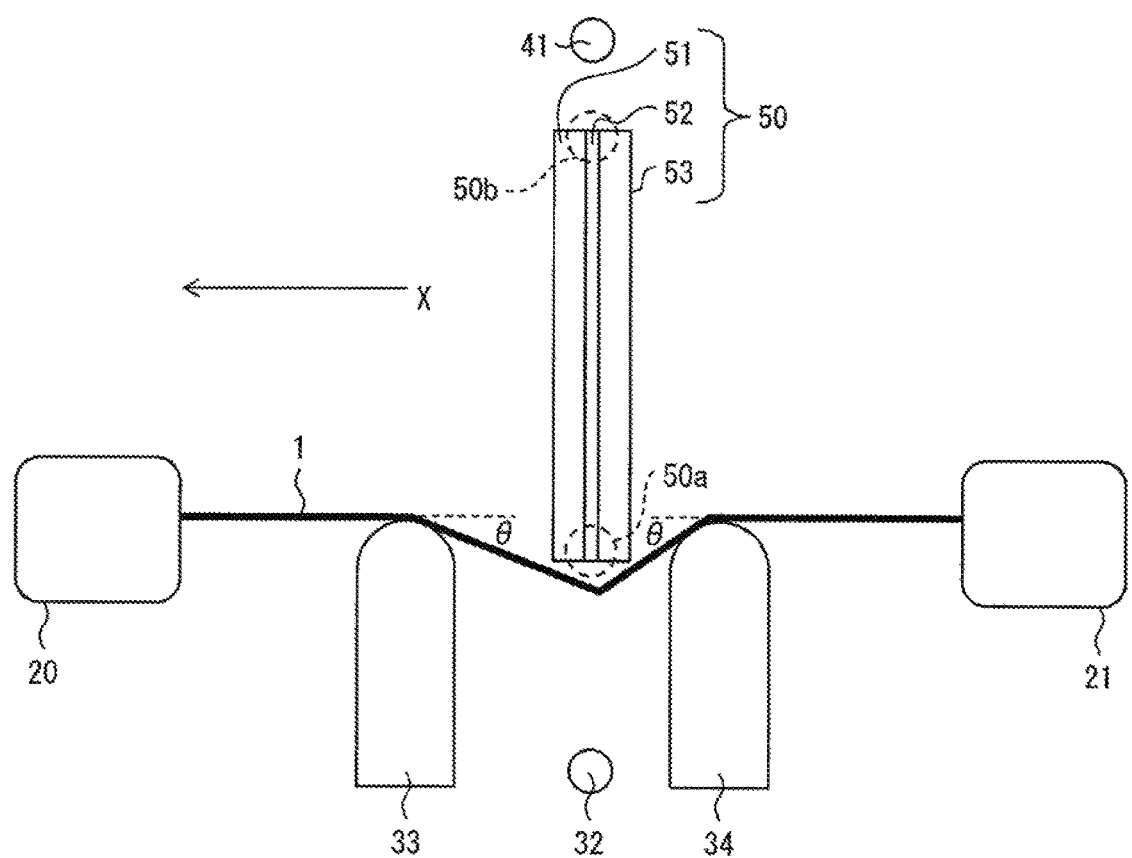
FIG. 4 is a cross-sectional view illustrating electrophoresis and transfer of a sample in an embodiment of the present invention.

Next, the flow of electrophoresis and transfer of sample in the biomolecule analyzer 100 will be explained by referencing FIG. 4. FIG. 4 is a cross-sectional via illustrating the electrophoresis and transfer of sample in the present embodiment. It should be noted that the anode buffer tank 30, cathode buffer tank 40, etc. are omitted in FIG. 4 for the purpose of explanation.

As shown in FIG. 4, during the electrophoresis and transfer of sample, the transfer membrane 1 is retained in a state arranged at a position opposing the first opening 50a by the clamps 20, 21 (adjuster, arm part). At this time, the transfer membrane 1 is supported from the back surface of the transfer membrane 1 (opposite side to the separation unit 50), by the guides 33, 34 provided at the bottom part of the anode buffer tank 30.

The guides 33 and 34 are provided at the bottom part of the anode buffer tank 30 so as to support the transfer membrane in the movement path on which the transfer membrane 1 moves. The guides 33 and 34 have a longitudinal direction that is orthogonal to the movement direction (X direction) of the transfer membrane 1, and are parallel to the longitudinal direction of the first opening 50a.

Then, by the separation unit 50 (side of the first opening 50a thereof) abutting the top surface of the transfer membrane 1 (side of the separation unit 50 thereof), the transfer membrane 1 is bent so that an opposite side to the separation unit 50 becomes convex. In this way, the transfer membrane 1 is supported by the guides 33 and 34, the separation unit 50 pushes this down to be bent so as to become convex downwards (opposite side to the separation unit 50). It is thereby possible for the tension to act on the transfer membrane 1, to cause the transfer membrane 1 to be in close contact with the first opening 50a. It is thereby possible to more appropriately perform transfer from the separation gel 52 to the transfer membrane 1.

In particular, by the guides 33 and 34 being respectively formed at positions interposing a position opposing the first opening 50a on the bottom part of the anode buffer tank 30 to form a pair, the transfer membrane 1 is supported by the guides 33 and 34 arranged at both sides of the separation unit 50, the separation unit 50 pushes this down to be bent so as to become convex downward (opposite side to the separation unit). It is thereby possible for tension to more uniformly act on the transfer membrane 1 to cause the transfer membrane 1 to be more uniformly in close contact with the opening 50a. It is thereby possible to more appropriately perform transfer from the separation gel 52 to the transfer membrane 1.

In more detail, the tension of the transfer membrane 1 upon transferring the sample from the separation gel 52 to the transfer membrane 1 is preferably a tension within the range of at least 1 N to no more than 12 N, and most preferably on the order of 6 N, for example. So long as the tension applied to the transfer membrane is the above range, it will be possible to transfer the sample from the separation gel 52 to the transfer membrane 1 with good sensitivity, as well as being able to prevent the transfer membrane 1 from being damaged by excessive tension.

Setting the tension of the transfer membrane 1 to the above-mentioned range can be appropriately realized by setting the slope angle θ of the transfer membrane 1 from a position contacting the guides 33 and 34 until a position contacting the first opening 50a to preferably at least 1° to no more than 60° downwards relative to a horizontal plane, and more preferably on the order of 10°. The tension of the transfer membrane 1 is defined by the above-mentioned slope angle; therefore, it is possible to set the tension of the transfer membrane 1 to the aforementioned range by setting the slope angle to within the aforementioned range.

It should be noted that, as mentioned above, the clamp frame 22 is arranged at positions interposing the transfer membrane 1 from lateral sides to the movement direction, and thus will not hinder the guides 33 and 34 from supporting the transfer membrane 1 from the back surface thereof.

Then, the sample is introduced to the separation gel 52 from the second opening 50b of the separation unit 50. In addition to biomolecules serving as the analysis target, it is preferable to add a visible molecular weight marker for confirming the progress of electrophoresis to the sample.

In the above state, separation is performed by electrophoresis of the sample. The control unit 68 controls the motor 62 to set the position of the transfer membrane 1 at the start position, and then flow electric current between the anode 32 and cathode 41 to start electrophoresis. The electric current value flowing between the anode 32 and cathode 41 is not particularly limited; however, it is preferably no more than 50 mA, and more preferably at least 20 mA to no more than 30 mA. It should be noted that it may control so that the electric current value becomes constant, may be controlled so that the voltage becomes constant, or the current and voltage may be controlled in other modes.

The transfer membrane 1 is moved gradually towards the X direction (substantially horizontal direction) by driving of the arm part (adjuster) by the drive unit, according to the progress of electrophoresis in the separation unit 50. The X direction is a direction orthogonal to the longitudinal direction of the first opening 50a. Although the movement speed of the transfer membrane 1 is not particularly limited, it is possible to set a pace of moving 5 to 10 cm in 60 to 120 minutes, for example.

Then, the sample dispensed according to electrophoresis from the first opening 50a (sample separated in separation gel 52) is adsorbed at positions (positions opposing the first opening 50a at the dispensed timing) according to the timing of dispensing to the transfer membrane 1. The separated sample is thereby transferred to the transfer membrane 1.

After transfer, it is possible to recover the transfer membrane 1, and supply to staining, immunoreaction (blotting and antigen-antibody reaction by Western blotting) or the like. Subsequently, the separation pattern of components transferred to the transfer membrane 1 is detected by a fluorescence detector. Such a fluorescence detector may be included in the biomolecule analyzer 100, whereby it is possible to automate the entire process of electrophoresis, transfer and detection.

By establishing a configuration in which the separation unit 50 is standing up substantially vertically in above way, it is possible for the separation unit 50 to be immersed in the buffer solution of at least one among the anode buffer tank 30 and cathode buffer tank 40, and thus liquid-cool the separation gel 52.

Then, in the case of configuring the biomolecule analyzer 100 in this way, (i) it is necessary to cause the transfer membrane 1 to move within the anode buffer tank 30, (ii) in the case of trying to arrange the drive unit upstream of the transfer membrane 1 as in the conventional technology, there is a risk of the buffer solution having scattered from the anode buffer tank 30 causing the durability of the drive unit to decline, and a risk of the drive unit becoming a hindrance to various operations on the biomolecule analyzer 100; however, (iii), with the present embodiment, by providing the drive unit under the anode buffer tank 30, and making the form of the arm part into a form that passes along the outer sides of the side walls of the anode buffer tank 30, wraps around the upper ends of the side walls and then links at the inner sides of the side walls, it is possible to cause the transfer membrane 1 to move successfully within the anode buffer tank 30, while avoiding a decline in the durability of the drive unit due to the buffer solution and the hindrance of various operations by the drive unit. It is thereby possible to provide a vertical-type direct-blot electrophoresis transfer device equipped with a suitable transfer membrane conveying mechanism.

Second Embodiment

Another embodiment of the present invention is as follows when explaining based on FIGS. 5 to 8. It should be noted that, for convenience of explanation, the members having the same function as members explained in the embodiment will be assigned the same reference numbers, and explanations thereof will be omitted.

In the biomolecule analyzer 100, the anode buffer tank 30, cathode buffer tank 40 and separation unit 50 may be made detachable from the biomolecule analyzer 100. Since it is thereby possible to remove and wash the anode buffer tank 30, cathode buffer tank 40 and separation unit 50, the first buffer solution tank can be easily washed without cleaning solution, etc. adhering to the drive unit.

Figure 5:
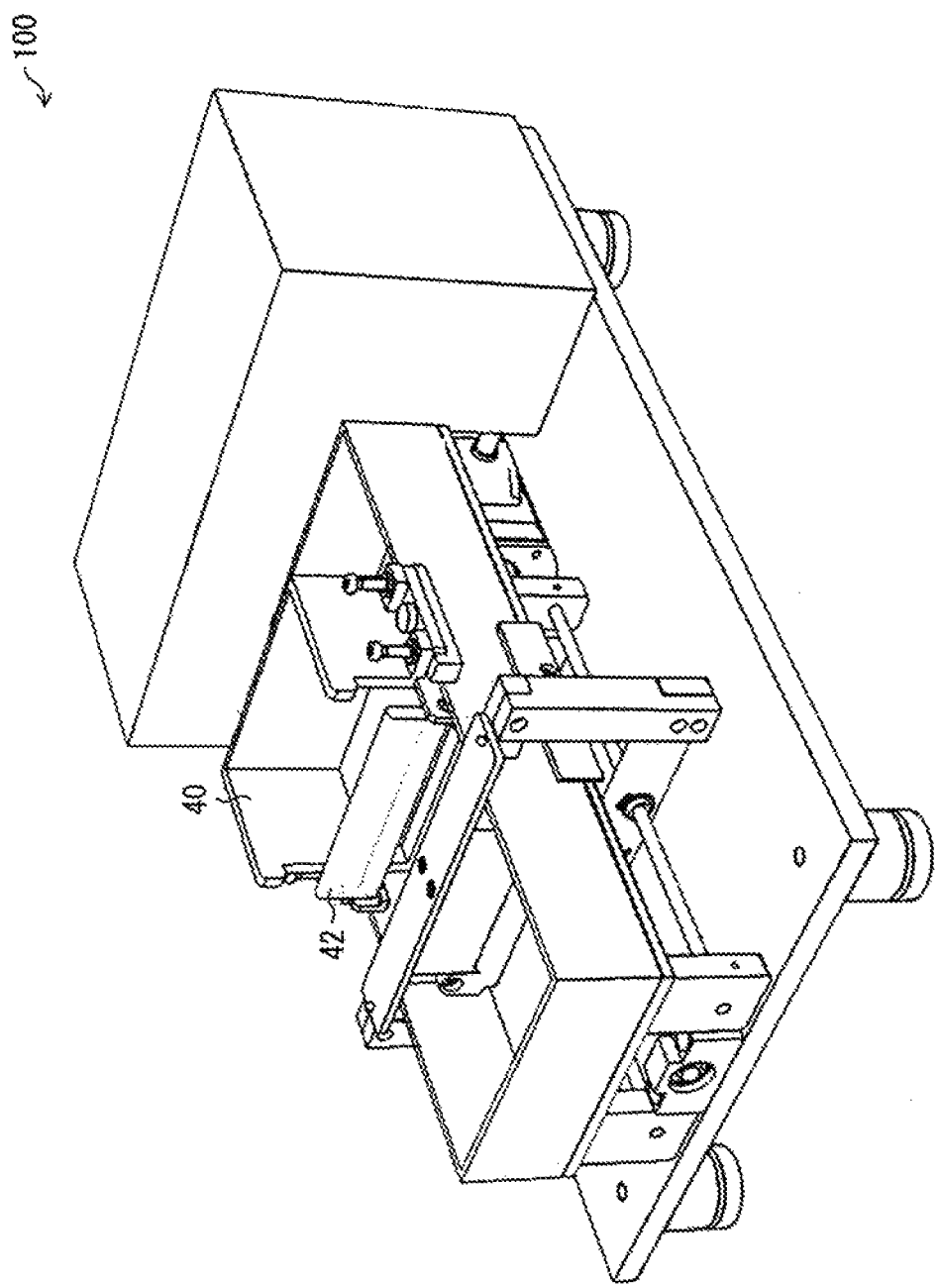
FIG. 5 is a perspective view showing an aspect of removing each member of a biomolecule analyzer according to an embodiment of the present invention.

FIG. 5 is a perspective view showing an aspect of removing the separation unit 50 from the biomolecule analyzer 100. The separation unit 50 is fixed to the cathode buffer tank 50 by a lock 42; therefore, it is possible to easily remove by releasing the lock 42. It should be noted that the separation unit 50 may be installed detachably to the cathode buffer tank 40, and the method thereof is not limited to the method of using the lock 42.

Figure 6:
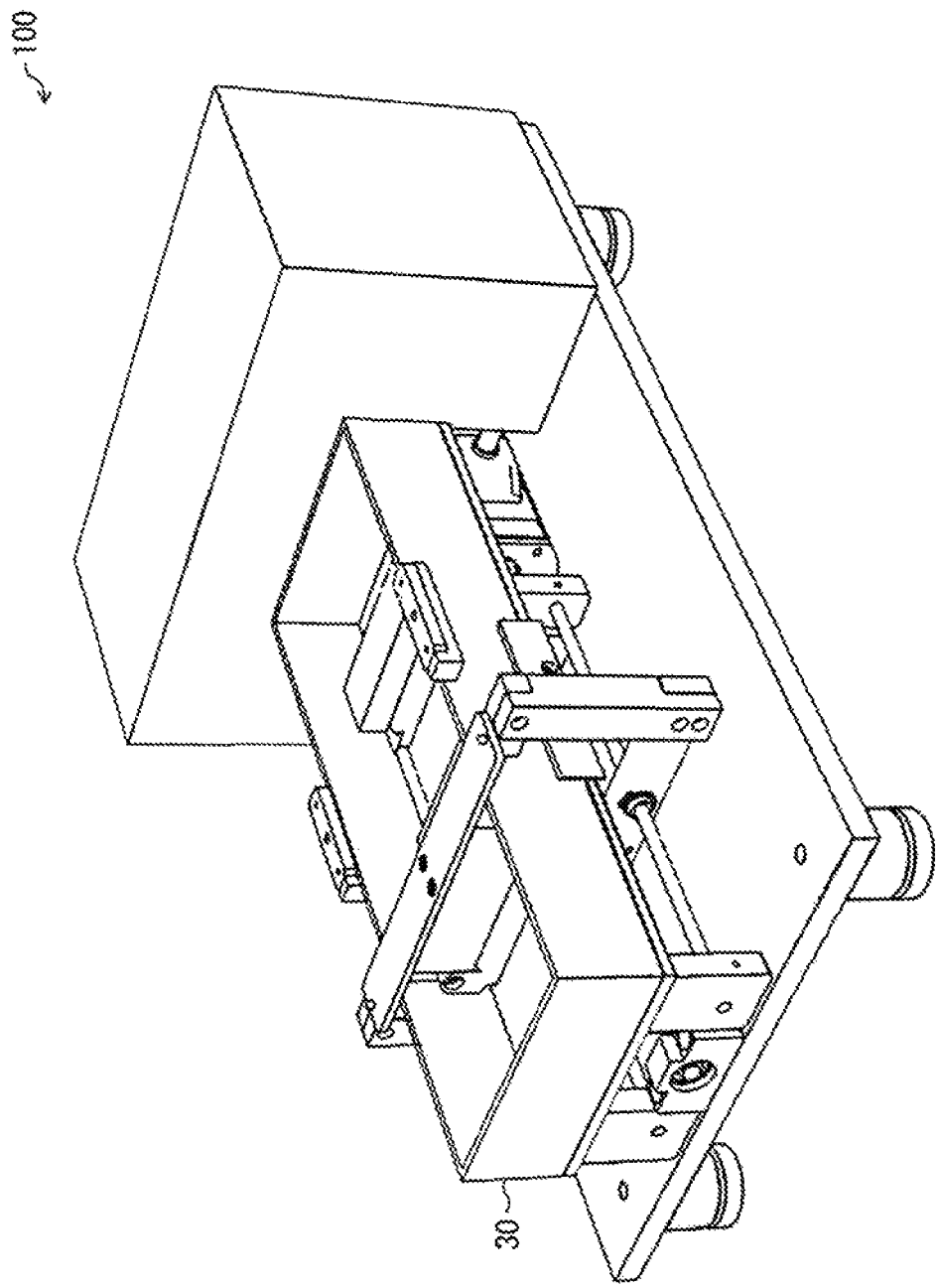
FIG. 6 is a perspective view showing an aspect of removing each member of a biomolecule analyzer according to an embodiment of the present invention.

FIG. 6 is a perspective view showing an aspect of further removing the cathode buffer tank 40 form the biomolecule analyzer 100. The cathode buffer tank 40 is not particularly limited; however, for example, it may be detachably fixed to the anode buffer tank 30 by way of treads, a lock or the like.

Figure 7:
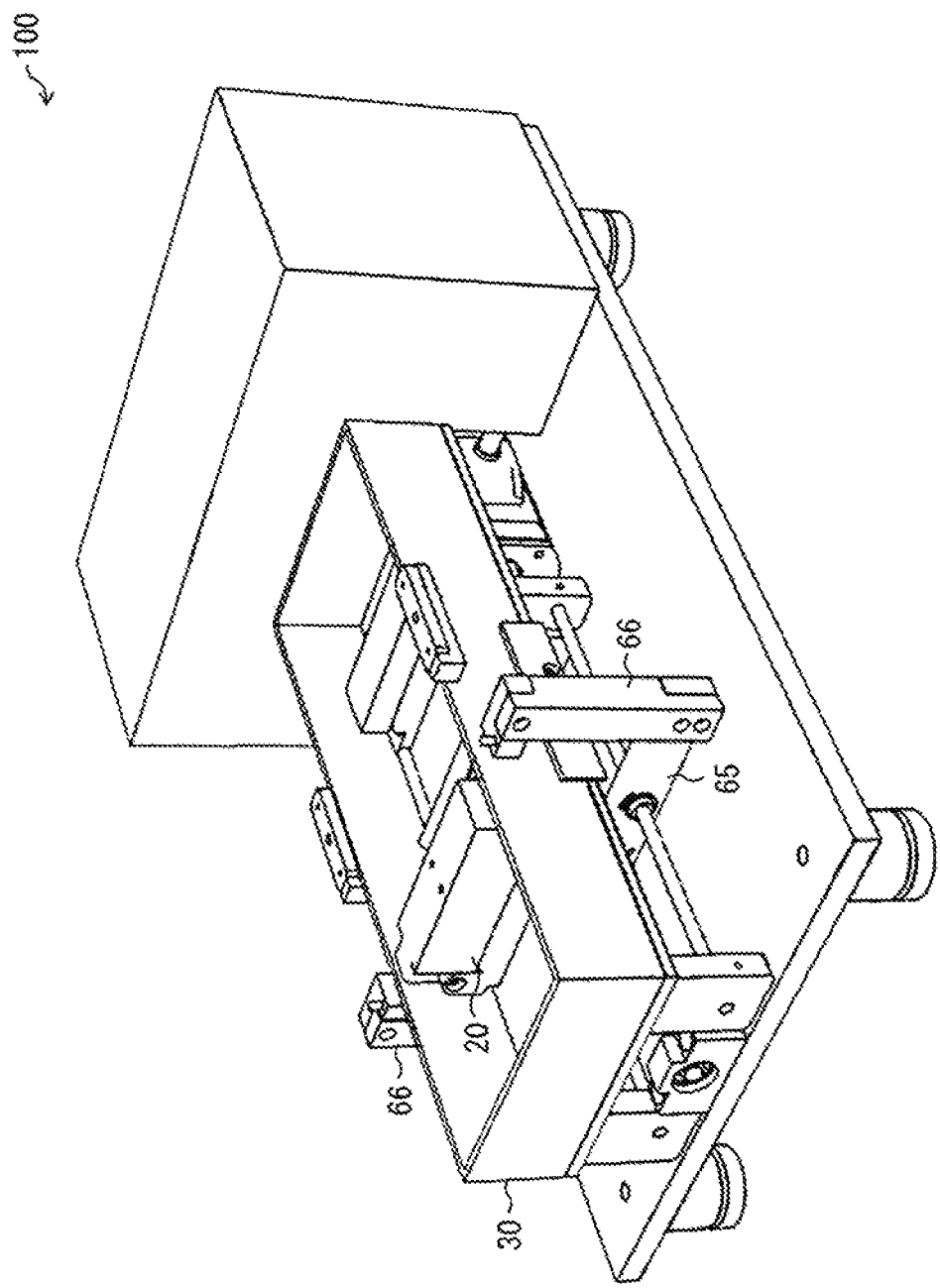
FIG. 7 is a perspective view showing an aspect of removing each member of a biomolecule analyzer according to an embodiment of the present invention.

FIG. 7 is a perspective view showing an aspect of further removing the carrier 23 from the biomolecule analyzer 100. The carrier 23 can be easily removed due to joining to the guide pole 66 and clamp 20 by fitting to each of the guide pole 66 and clamp 20. It should be noted that the carrier 23 may be detachable from at least the drive unit, and for example, the guide pole 66 may be made separable from the shaft holder 65.

Figure 8:
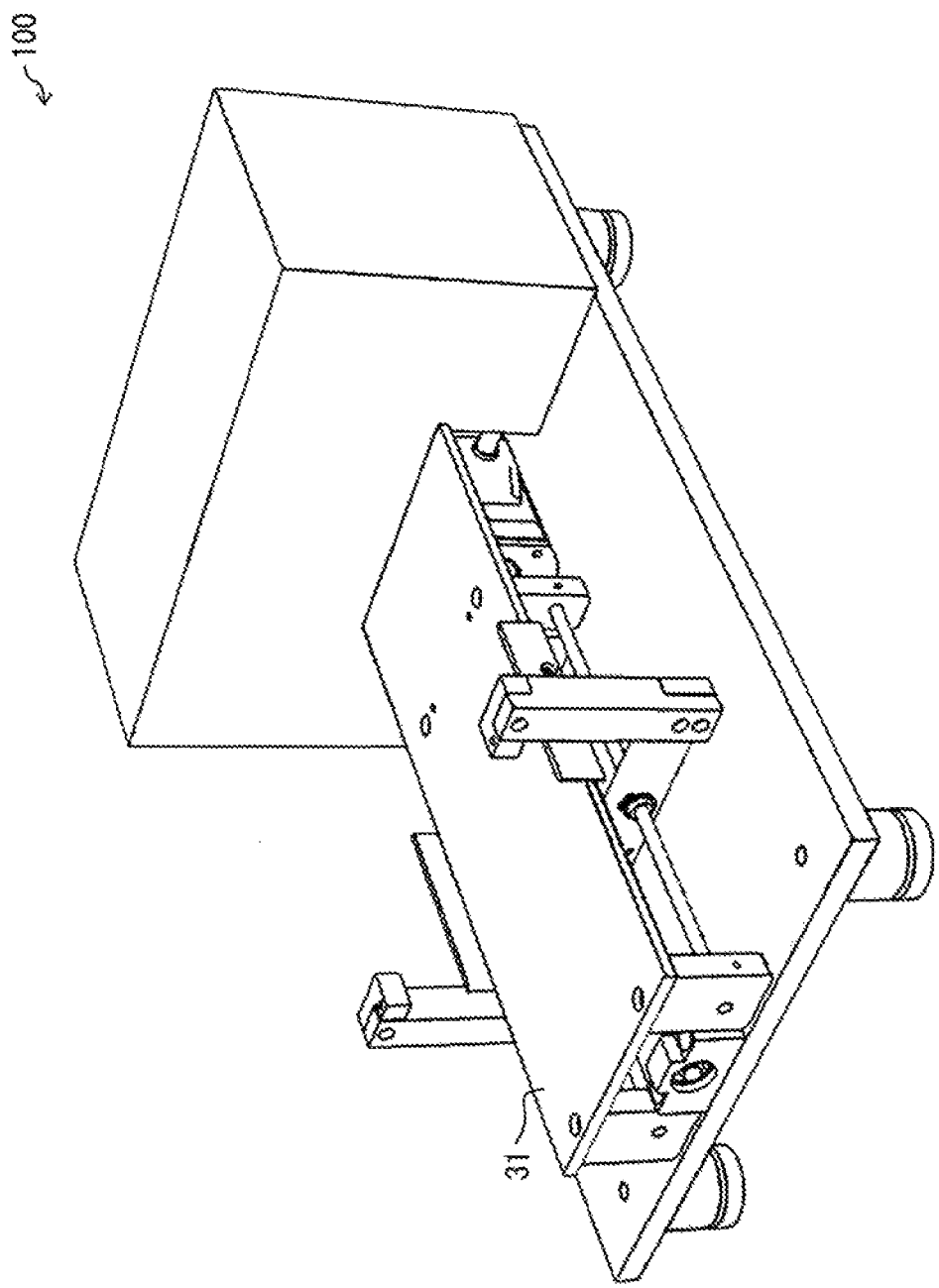
FIG. 8 is a perspective view showing an aspect of removing each member of a biomolecule analyzer according to an embodiment of the present invention.

FIG. 8 is a perspective view showing an aspect of further removing the anode buffer tank 30 from the biomolecule analyzer 100. As mentioned above, with the present embodiment, since it is possible to separate the carrier 23, which is a portion of the arm part that wraps around the top ends of the side walls of the anode buffer tank 30, from the drive unit, it is possible to easily detach the anode buffer tank 30. The anode buffer tank 30 is not particularly limited; however, for example, it may be detachably fixed to the table 31 by fitting together.

Third Embodiment

Another embodiment of the present invention is as follows when explaining based on FIG. 9. It should be noted that, for convenience of explanation, the members having the same function as members explained in the embodiment will be assigned the same reference numbers, and explanations thereof will be omitted.

Figure 9:
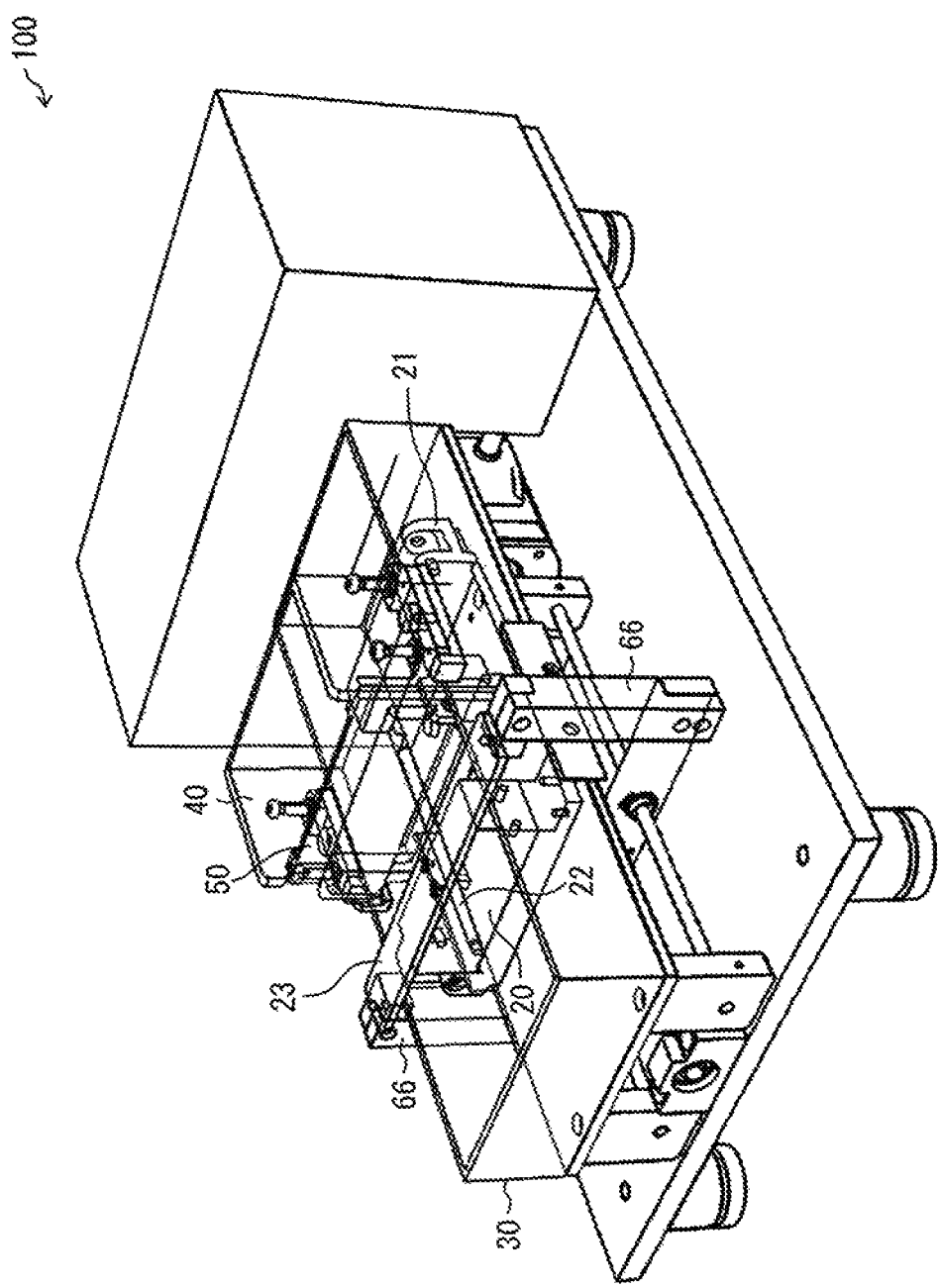
FIG. 9 is a perspective view showing an outline configuration of a biomolecule analyzer according to an embodiment of the present invention.

FIG. 9 is a perspective view showing an outline configuration of a biomolecule analyzer 100 according to the present embodiment. As shown in FIG. 9, with the present embodiment, the anode buffer tank 30, cathode buffer tank 40 and separation unit 50, for example, are configured so that the entirety or portions thereof are made transparent using a transparent resin, glass or the like. In addition, the lid covering the entirety during the aforementioned operation is also configured so as to be transparent. It should be noted that, preferably, the arm part (clamps 20, 21, clamp frame 22, carrier 23 and guide poles 66) may further be configured so that the entirety or portion thereof is transparent. It is thereby possible to observe the states of the separation gel 52 and transfer membrane 1 during operation of the device. It is thereby possible to confirm the movement of the visible marker by the naked eye, for example.

Fourth Embodiment

Another embodiment of the present invention is as follows when explaining based on FIG. 10. It should be noted that, for convenience of explanation, the members having the same function as members explained in the embodiment will be assigned the same reference numbers, and explanations thereof will be omitted. The present embodiment has a different configuration for the adjuster than the first embodiment, and other configurations thereof are the same as the first embodiment. Hereinafter, the difference in the configuration of the adjuster will be explained.

Figure 10A:
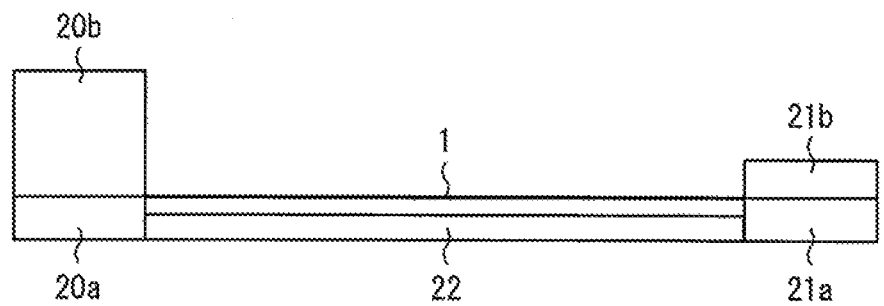
FIG. 10 is a cross-sectional view showing an outline configuration of an adjuster in an embodiment of the present invention.

FIG. 10(*a*) is a cross-sectional view showing the configuration of the adjuster in the first embodiment, and (*b*) is a cross-sectional view showing the configuration of the adjuster in the present embodiment. Both adjusters include a clamp (first fixing part) 20 that fixes an end (first end) that is forward in the movement direction of the transfer membrane 1, a clamp (second fixing part) 21 that fixes an end (second end) that is rearward in the movement direction of the transfer membrane 1, and a clamp frame (connection part) 22 that connects the clamp 20 and clamp 21.

Figure 10B:
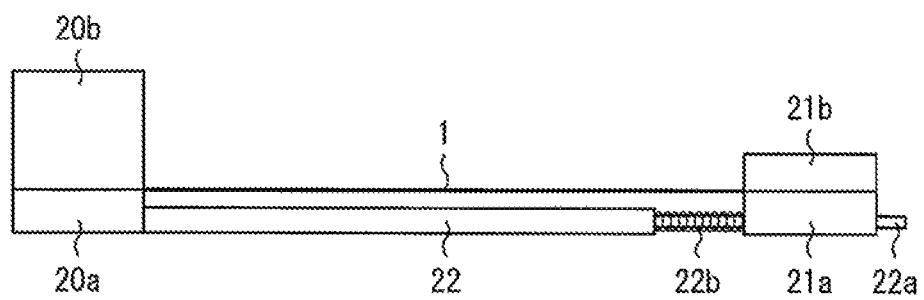

Herein, with the adjuster according to the present embodiment, a portion of the clamp frame 22 on the side of the clamp 21 becomes an insertion part 22a having a narrow diameter, and the insertion part 22a is inserted into the clamp 21, as shown in FIG. 10(b). The clamp 21 is thereby configured to be able to slide along the clamp frame 22. Furthermore, an elastic body 22b is provided at a position interposed by the clamp frame 22 and clamp 21, and the clamp 20 and clamp 21 connected to the clamp frame 22 are biased in directions facing away from each other by the elastic force of the elastic body 22b. Herein, for example, in a state bringing together the clamp 20 and clamp 21 against the above-mentioned elastic force, if releasing from a state fixing both ends of the transfer membrane 1 to the clamp 20 and 21, respectively, and bringing together the clamp 20 and clamp 21, it is possible to establish a state in which both ends of the transfer membrane 1 are drawn in a direction facing away from each other, imparting a constant tension to the transfer membrane 1 to be tight. If a state in which the transfer membrane 1 is loose, when causing the transfer membrane 1 to move, the interval between the transfer membrane 1 and first opening 50a may become large, and the transfer result may be blurred; however, according to the above-mentioned configuration, since it is possible to establish the transfer membrane 1 in a tightened state, favorable transfer results can be obtained.

In particular, as shown in FIG. 4, in a state in which the transfer membrane 1 is supported by the guides 33 and 34, and the separation unit 50 is pushing this down to be bent so as to become convex (opposite side to the separation unit 50) downwards, the transfer membrane 1 comes to be pressed to the first opening 50a to try to return to a state not bent, by the transfer membrane 1 being maintained in a state tightened by the elastic body 22b. It is thereby possible to force the transfer membrane 1 so as not to distance from the first opening 50a and obtain favorable transfer results.

It should be noted that, so long as the elastic body 22b biases the clamps 20 and 21 in directions facing away from each other by way of the elastic force thereof, the material, arrangement, etc. thereof are not particularly limited; however, it is preferable to configure by a material not inducing electrolysis, or to coat with a material that does not induce electrolysis. For example, the elastic body 22b can be a spring for which the material is constituted from resin that does not induce electrolysis, or a metal coated with resin. The elastic body 22b may be an elastic body such as a sponge or rubber.

The present invention is not to be limited the aforementioned respective embodiments, with various modifications being possible within the scope indicated by the claims, and embodiments obtained by appropriately combining the technical means disclosed in each of the different embodiments are also included in the technical scope of the present invention. Furthermore, it is possible to form novel technical features by combining the technical means disclosed in each of the respective embodiments.

INDUSTRIAL APPLICABILITY

The present invention is applicable in the production field of analysis equipment for biomolecules, etc. and the analysis field of biomolecules, etc.

EXPLANATION OF REFERENCE NUMERALS 1 transfer membrane
20 clamp (arm part, first fixing part)
21 clamp (arm part, second fixing part)
22 clamp frame (arm part, connection part)
22b elastic body
23 carrier (arm part, portion going around upper ends of side walls, second portion)
30 anode buffer tank (first buffer solution tank)
31 table
32 anode (first electrode)
34, 35 guide (support member)
40 cathode buffer tank (second buffer solution tank)
41 cathode (second electrode)
42 lock
50 separation unit
50a first opening
50b second opening
51, 53 insulating plate
52 separation gel (separation medium)
62 motor (drive unit)
63 ball screw (drive unit)
64 guide shaft (drive unit)
65 shaft holder (drive unit)
66 guide pole (arm part, first portion)
68 control unit
10 biomolecule analyzer

The invention claimed is:

1. A biomolecule analyzer comprising:
a first buffer solution tank;
a second buffer solution tank that is disposed above the first buffer solution tank;
a separation unit in which a separation medium is stored, having a first opening that opens within the first buffer solution tank and a second opening that opens within the second buffer solution tank, and the separation unit is standing up in a substantially vertical direction;
an arm part that retains a transfer membrane disposed at a position opposing the first opening; and
a drive unit that is provided under the first buffer solution tank, and drives the arm part in a substantially horizontal direction,
wherein the arm part passes along outer sides of side walls of the first buffer solution tank, wraps around upper ends of the side walls, and links at inner sides of the side walls.

2. The biomolecule analyzer according to claim 1,
wherein the transfer membrane has a first end that is forward in a movement direction of the arm part and a second end that is rearward in the movement direction of the arm part, and
wherein the arm part includes a first fixing part that fixes the first end, a second fixing part that fixes the second end, and an elastic body that biases the first fixing part and the second fixing part in directions facing away from each other.

3. The biomolecule analyzer according to claim 2,
wherein a support member for supporting the transfer membrane from an opposite side of the transfer membrane to the separation unit is provided at a bottom part of the first buffer solution tank, and
wherein the transfer membrane is bent by the separation unit so that an opposite side to the separation unit becomes convex.

4. The biomolecule analyzer according to claim 3,
wherein the support member is on the bottom part and includes a pair of members interposing a position opposing the first opening.

5. The biomolecule analyzer according to claim 1,
wherein the transfer membrane has a first end that is forward in a movement direction of the arm part, and a second end that is rearward in the movement direction of the arm part, and
wherein the arm part includes a first fixing part that fixes the first end, a second fixing part that fixes the second end, and a connection part that connects the first fixing part and the second fixing part to be separated by a predetermined distance.

6. The biomolecule analyzer according to claim 5, wherein the connection part includes a pair of parts disposed at positions to interpose the transfer membrane laterally relative to the movement direction of the arm part.

7. The biomolecule analyzer according to claim 1,
wherein a support member that supports the transfer membrane from an opposite side to the separation unit of the transfer membrane is provided to a bottom part of the first buffer solution tank, and
wherein the transfer membrane is bent by the separation unit so that an opposite side to the separation unit becomes convex.

8. The biomolecule analyzer according to claim 7, wherein the support member includes a pair of members respectively on the bottom part to interpose a position that opposes the first opening.

9. The biomolecule analyzer according to claim 8, wherein a slope angle of the transfer membrane from a position contacting the support member until a position contacting the first opening is at least 14 and no more than 60 downwards relative to a horizontal plane.

10. The biomolecule analyzer according to claim 1,
wherein a portion of the arm part that wraps around the upper ends of the side walls is detachable from the drive unit, and
wherein the first buffer solution tank is detachable from the biomolecule analyzer.

11. The biomolecule analyzer according to claim 10, wherein the arm part is linked to the drive unit, and has a first portion extending at outer sides of the side walls until a position aligning with upper ends of the side walls, and a second portion that fits with the first portion, and extends to an inner side of the side walls by spanning the upper ends of the side walls.

12. The biomolecule analyzer according to claim 1,
wherein the first buffer solution tank, the second buffer solution tank and the separation unit are transparent.

13. The biomolecule analyzer according to claim 1, wherein a first electrode is disposed in the first buffer solution tank,
wherein a second electrode is disposed in the second buffer solution tank, and
wherein the transfer membrane is disposed so as to be interposed between the first opening and the first electrode.

14. The biomolecule analyzer according to claim 1,
wherein the separation unit is mounted to be detachable from the second buffer solution tank, and
wherein the second buffer solution tank is mounted to be detachable from the first buffer solution tank.

* * * * *